(12) United States Patent
Yelin et al.

(10) Patent No.: US 10,531,790 B2
(45) Date of Patent: *Jan. 14, 2020

(54) METHOD AND SYSTEM OF SPECTRALLY ENCODED IMAGING

(71) Applicant: TECHNION RESEARCH & DEVELOPMENT FOUNDATION LIMITED, Haifa (IL)

(72) Inventors: Dvir Yelin, Haifa (IL); Avraham Abramov, Pardes Hana (IL)

(73) Assignee: TECHNION RESEARCH & DEVELOPMENT FOUNDATION LTD., Haifa (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/461,404

(22) Filed: Aug. 17, 2014

(65) Prior Publication Data

US 2015/0105622 A1 Apr. 16, 2015

Related U.S. Application Data

(63) Continuation of application No. 12/816,395, filed on Jun. 6, 2010, now Pat. No. 8,812,087.

(Continued)

(51) Int. Cl.
*A61B 1/07* (2006.01)
*G01N 21/55* (2014.01)
(Continued)

(52) U.S. Cl.
CPC .......... *A61B 1/07* (2013.01); *A61B 1/00163* (2013.01); *A61B 5/0084* (2013.01); *G01J 3/02* (2013.01); *G01J 3/024* (2013.01); *G01J 3/0208* (2013.01); *G01J 3/0218* (2013.01); *G01J 3/0256* (2013.01); *G01N 21/55* (2013.01); *G01N 21/645* (2013.01); *G01J 3/2823* (2013.01);
(Continued)

(58) Field of Classification Search
CPC ... A61B 5/0075; A61B 5/0084; A61B 5/0086; A61B 5/0071; A61B 1/043; A61B 1/07; A61B 1/00163; G01J 3/0218; G01J 3/0256; G01J 3/024; G01J 3/02; G01J 3/0208; G01J 3/2823; G01N 21/645; G01N 21/55; G01N 2021/6484; G01N 2021/6417; G01N 2201/084
USPC .................................................. 600/473–480
See application file for complete search history.

(56) References Cited

U.S. PATENT DOCUMENTS 5,293,872 A * 3/1994 Alfano ................. A61B 5/0071
600/475
5,434,669 A * 7/1995 Tabata ............... G01B 11/2441
356/241.5

(Continued)

*Primary Examiner* — Sanjay Cattungal
(74) *Attorney, Agent, or Firm* — Alphapatent Associates, Ltd; Daniel J. Swirsky

(57) ABSTRACT

A spectrally encoded imaging device having a light transmission path arrangement which propagates light to illuminate a target object, a light collection path arrangement having a light collection waveguide which propagates a spectrally encoded portion of the light from the target object to a detector which forms an image of the target object accordingly, and a diffractive element which spectrally disperses at least one of the light and the spectrally encoded portion. The light transmission path arrangement and the light collection path arrangement are optically isolated from one another.

19 Claims, 8 Drawing Sheets

Related U.S. Application Data

(60) Provisional application No. 61/187,335, filed on Jun. 16, 2009.

(51) Int. Cl.
| | | |
|---|---|---|
| *G01N 21/64* | (2006.01) | |
| *G01J 3/02* | (2006.01) | |
| *A61B 5/00* | (2006.01) | |
| *A61B 1/00* | (2006.01) | |
| *G01J 3/28* | (2006.01) | |

(52) U.S. Cl.
CPC .............. *G01N 2021/6417* (2013.01); *G01N 2021/6484* (2013.01); *G01N 2201/084* (2013.01)

(56) References Cited

U.S. PATENT DOCUMENTS

| | | | | |
|---|---|---|---|---|
| 5,441,053 | A * | 8/1995 | Lodder | A61B 5/0086 600/473 |
| 5,713,364 | A * | 2/1998 | DeBaryshe | A61B 1/00059 250/461.2 |
| 6,110,106 | A * | 8/2000 | MacKinnon | A61B 5/0071 600/160 |
| 6,233,373 | B1 * | 5/2001 | Askins | G01J 3/02 356/451 |
| 6,341,036 | B1 * | 1/2002 | Tearney | A61B 5/0066 359/209.1 |
| 6,564,088 | B1 * | 5/2003 | Soller | A61B 5/0075 600/478 |
| 6,615,071 | B1 * | 9/2003 | Casscells, III | A61B 5/0086 600/474 |
| 6,816,743 | B2 * | 11/2004 | Moreno | A61B 5/0075 382/128 |
| 7,267,648 | B2 * | 9/2007 | Hasegawa | A61B 1/00188 600/168 |
| 7,570,988 | B2 * | 8/2009 | Ramanujam | A61B 5/0091 356/303 |
| 7,809,226 | B2 * | 10/2010 | Bouma | G02B 6/02042 385/123 |
| 7,925,133 | B2 * | 4/2011 | Bouma | G02B 6/02042 385/126 |
| 8,280,351 | B1 * | 10/2012 | Ahmed | H04L 63/102 380/229 |
| 2002/0168317 | A1 * | 11/2002 | Daighighian | A61K 49/18 424/1.11 |
| 2004/0024298 | A1 * | 2/2004 | Marshik-Geurts | A61B 5/0075 600/326 |
| 2004/0210113 | A1 * | 10/2004 | Hasegawa | A61B 1/00188 600/181 |
| 2005/0023356 | A1 * | 2/2005 | Wiklof | G06K 7/10851 235/462.42 |
| 2006/0013544 | A1 * | 1/2006 | Bouma | G02B 6/02042 385/116 |
| 2007/0035818 | A1 * | 2/2007 | Bahatt | G01N 21/253 359/366 |
| 2007/0076220 | A1 * | 4/2007 | Kawahara | A61B 5/0066 356/511 |
| 2007/0233396 | A1 * | 10/2007 | Tearney | A61B 5/0062 702/19 |
| 2007/0239035 | A1 * | 10/2007 | Nakabayashi | G01J 3/02 600/476 |
| 2007/0299312 | A1 * | 12/2007 | Hasegawa | A61B 1/00188 600/160 |
| 2008/0004496 | A1 * | 1/2008 | Hasegawa | A61B 1/00188 600/168 |
| 2008/0007716 | A1 * | 1/2008 | Igarashi | G01J 3/02 356/72 |
| 2008/0058629 | A1 * | 3/2008 | Seibel | A61B 1/0008 600/368 |
| 2008/0097225 | A1 * | 4/2008 | Tearney | A61B 18/22 600/478 |
| 2010/0067004 | A1 * | 3/2010 | Nagashima | G01J 3/02 356/326 |
| 2010/0198081 | A1 * | 8/2010 | Hanlin | A61B 5/0062 600/478 |
| 2011/0178379 | A1 * | 7/2011 | Dudhia | A61B 5/0075 600/310 |
| 2011/0295541 | A1 * | 12/2011 | Yu | G01J 3/02 702/104 |
| 2011/0313299 | A1 * | 12/2011 | Brennan, III | A61B 5/0086 600/478 |
| 2012/0144035 | A1 * | 6/2012 | Waites | H04L 63/0876 709/225 |
| 2013/0066215 | A1 * | 3/2013 | Tearney | A61B 18/22 600/478 |
| 2013/0100455 | A1 * | 4/2013 | Tearney | A61B 5/0062 356/479 |
| 2013/0176571 | A1 * | 7/2013 | Tearney | A61B 5/0062 356/456 |
| 2013/0198071 | A1 * | 8/2013 | Jurss | G06Q 20/108 705/42 |
| 2014/0189808 | A1 * | 7/2014 | Mahaffey | H04L 63/083 726/4 |
| 2014/0378846 | A1 * | 12/2014 | Hosoda | A61B 5/6876 600/478 |
| 2015/0213238 | A1 * | 7/2015 | Farha | G06F 21/10 726/30 |
| 2015/0262224 | A1 * | 9/2015 | Brown | G06Q 30/0246 705/14.45 |

* cited by examiner

METHOD AND SYSTEM OF SPECTRALLY ENCODED IMAGING

CROSS-REFERENCE TO RELATED APPLICATIONS

This application is a continuation of U.S. patent application Ser. No. 12/816,395, filed Jun. 16, 2010, which claims the benefit of priority from U.S. Provisional Patent Application No. 61/187,335, filed Jun. 16, 2009, the contents of which are incorporated herein by reference in their entirety.

FIELD AND BACKGROUND OF THE INVENTION

The present invention, in some embodiments thereof, relates to methods and systems of imaging and, more particularly, but not exclusively, to methods and systems of spectral imaging using optical fibers.

Sub-millimeter diameter endoscopes are being examined for usage in many clinical applications that require minimal tissue damage. The harsh size constraints result with reduction of the number of imaging fibers in fiber bundle endoscopes and limit the frame rate of lateral scanning single optical-fiber probes. Recently, a new method termed spectrally encoded endoscopy (SEE) was introduced, utilizing a single optical fiber and miniature diffractive optics to encode transverse reflections from a sample, see Tearney, G. J., M. Shishkov, and B. E. Bouma, Spectrally encoded miniature endoscopy. Opt. Lett., 27(6): p. 412-414, 2002 and Yelin, D., et al., Three-dimensional miniature endoscopy. Nature, 443 (7113): p. 765-765, 2006, which is incorporated herein by reference. Since rapid lateral scanning is not required, SEE uses slow axis scanning by probe rotation, and is thus capable of high quality imaging through ultra-miniature, single fiber endoscopic probes.

SEE is capable of imaging through ultra-miniature flexible endoscopic probes by encoding transverse reflections which are propagated, via a single optical fiber and miniature diffractive optics, from an imaged object, such as an intrabody surface or an organ. Using low coherence interferometry, recent works have demonstrated that SEE is capable of video rate, three-dimensional imaging of surface and subsurface tissue structures, as well as Doppler imaging of acoustic vibrations and flow, see for example any of the following references which are incorporated herein by reference: Tearney, G. J., M. Shishkov, and B. E. Bouma, Spectrally encoded miniature endoscopy. Opt. Lett., 27(6): p. 412-414, 2002; Yelin, D., et al., Three-dimensional miniature endoscopy. Nature, 443(7113): p. 765-765, 2006; Yelin, D., et al., Spectral-domain spectrally encoded endoscopy. Optics Express, 15(5): p. 2432-2444, 2007; Yelin, D., B. E. Bouma, and G. J. Tearney, Volumetric sub-surface imaging using spectrally encoded endoscopy. Optics Express, 16(3): p. 1748-1757, 2008; Yelin, D., et al., Doppler imaging using spectrally encoded endoscopy. Optics Express, 16(19): p. 14836-14844, 2008; and van Engen, A. G., S. A. Diddams, and T. S. Clement, Dispersion Measurements of Water with White-Light Interferometry. Appl. Opt., 37: p. 5679-5686, 1998.

SUMMARY OF THE INVENTION

According to some embodiments of the present invention there is provided a spectrally encoded imaging device. The spectrally encoded imaging device comprises a light transmission path arrangement which propagates light to illuminate a target object, a light collection path arrangement having a light collection waveguide which propagates a spectrally encoded portion of the light from the target object to a detector which forms an image of the target object accordingly, and a diffractive element which spectrally disperses at least one of the light and the spectrally encoded portion. The light transmission path arrangement and the light collection path arrangement are optically isolated from one another.

Optionally, the spectrally encoded portion is a reflection from the light from the target object.

Optionally, the spectrally encoded portion is a portion of the light which passes via the target object.

Optionally, the spectrally encoded portion is a light emitted from the light from a fluorescence material of the target object.

Optionally, the spectrally encoded imaging device further comprises a light source for generating the light.

More optionally, the light source is a miniature light source placed on the tip of the imaging device.

Optionally, the light transmission path arrangement comprises a light transmission waveguide for propagating the broadband light to illuminate the target object.

More optionally, the diffractive element is a grating slanted in relation to the axis of the light transmission waveguide.

Optionally, the diffractive element is mounted on the tip of the light collection waveguide.

More optionally, the light source is placed to illuminate the target object from a certain side of the target object and the light collection path arrangement being set to collect the portion from an opposing side of the target object.

Optionally, the collection path arrangement is set to collect the portion on a first axis; further comprising an optical arrangement for directing the light to illuminate the target object from the first axis.

Optionally, the light is a broadband light.

Optionally, the light is a narrowband light and the target object comprising a fluorescence material which emits, when excited by the narrowband light, a broadband light.

Optionally, the light transmission path arrangement is external to an intrabody space confining the target object.

According to some embodiments of the present invention there is provided a method of imaging a target object. The method comprises maneuvering a guiding tool having a light collection path arrangement therealong and at least one diffractive element mounted on its tip to a target space via at least one tubular lumen, propagating light toward a target object in the target space via a light transmission path arrangement, using the diffractive element for spectrally disperse at least one of the light and a portion thereof from the target object, propagating the portion via the light collection path arrangement to a detector which forms an image of the target object accordingly, and wherein the light transmission path arrangement and the light collection path arrangement are optically isolated from one another.

Optionally, the guiding tool is a microcatheter, the target space is an intrabody space, and the target object is a tissue surface.

Optionally, the propagating light comprises directly illuminating the target object with the light.

Optionally, the method is performed during a procedure selected from a group consisting of: endoscopy, bronchoscopy, rhinoscopy, nasopharyngoscopy, laryngoscopy, and nasolaryngoscopy.

Optionally, the using the diffractive element comprising spectrally disperse the light and using the spectrally dispersed light to illuminate the target object.

Optionally, maneuvering comprising maneuvering a light transmission path arrangement to propagate the light toward a certain side of the target object, the light collection path arrangement being placed to collect the portion from an opposing side of the target object.

According to some embodiments of the present invention there is provided a spectrally encoded imaging device. The spectrally encoded imaging device comprises a light transmission waveguide which propagates light to illuminate a target object, a light collection waveguide which propagates a spectrally encoded portion of the light from the target object to a detector which forms an image of the target object accordingly, an elongated tubular guiding member sized and shaped for being guided along a tubular lumen, toward an inner target space, and having an inner lumen for covering the light transmission waveguide and the light collection waveguide and a distal end, and a diffractive element, mounted in the distal end, which spectrally disperses at least one of the light and the spectrally encoded portion. The waveguides are optically isolated from one another.

According to some embodiments of the present invention there is provided a spectrally encoded imaging device. The spectrally encoded imaging device comprises a light transmission path arrangement which propagates spectrally encoded light to illuminate a target object, and a light collection path arrangement having a light collection waveguide which propagates a portion of the spectrally encoded light from the target object to a detector which forms an image of the target object accordingly. The light transmission path arrangement and the light collection path arrangement are optically isolated from one another.

Optionally, the light transmission path having a diffractive element which spectrally disperses a broadband light to provide the spectrally encoded light.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF EMBODIMENTS OF THE INVENTION

Figure 1:
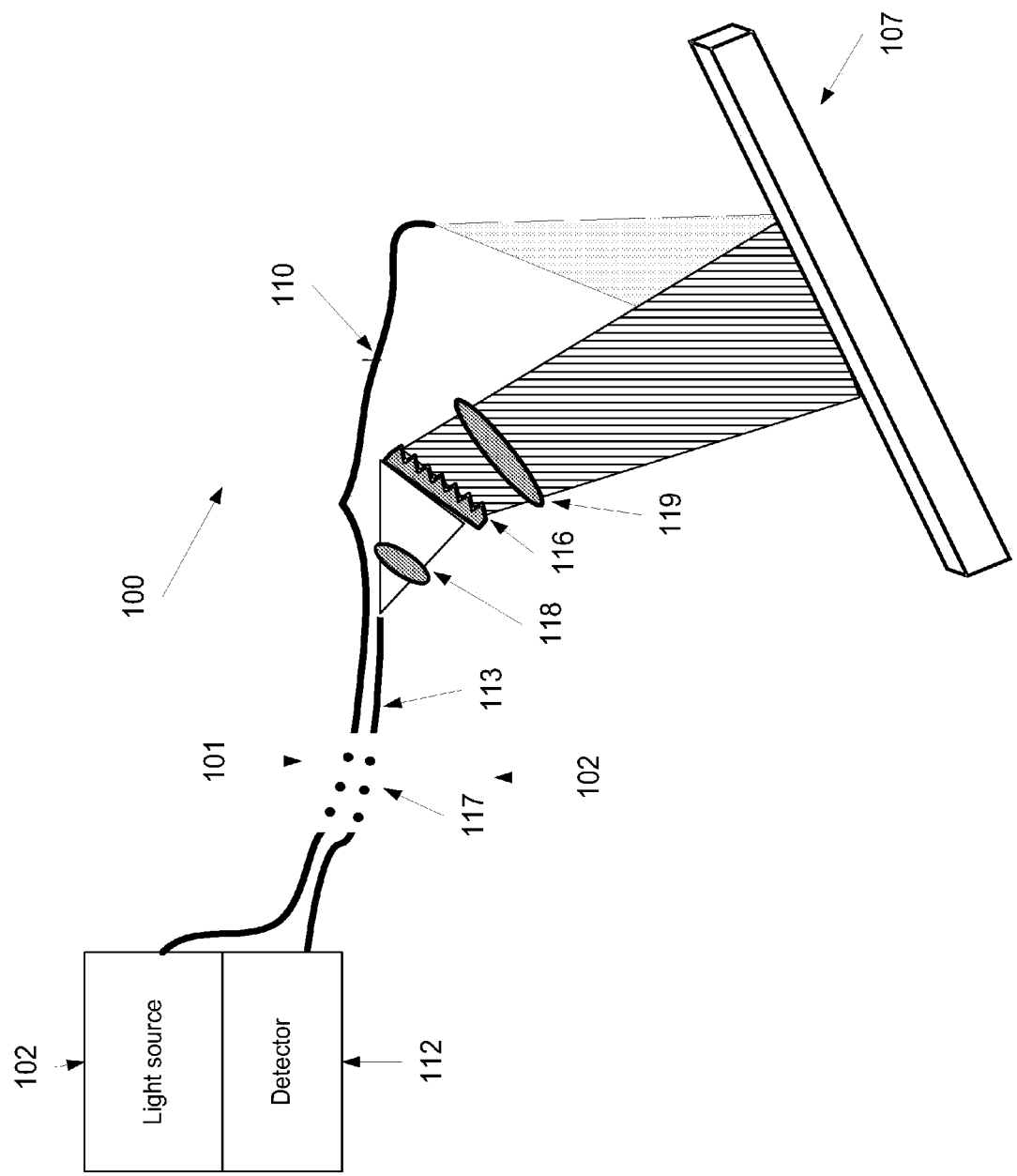
FIG. 1 is a schematic illustration of a spectrally encoded imaging device having light transmission and light collection path arrangements which are optically separated and/or isolated from one another, according to some embodiments of the present invention.

The present invention, in some embodiments thereof, relates to methods and systems of imaging and, more particularly, but not exclusively, to methods and systems of spectrally encoded imaging using optical fibers.

According to some embodiments of the present invention there is provided devices and methods for spectrally encoded imaging of a target object, such as an endoscope or borescope procedures, in which a light collection path arrangement and a light transmission path arrangement are optically isolated from one another so that spectrally encoded light from the target object may be propagated separately from light source, optionally broadband, which is used for illuminating the target object. The imaging device includes a light transmission path arrangement which propagates light to illuminate a target surface. The path arrangement optionally includes a waveguide, such as an optical fiber for propagating the illumination light to the target space, for example from a light source such as a broadband light source. The device further includes a light collection path arrangement which propagates a spectrally encoded portion of the light, for example a reflection or a passing through light, from the target object, to a detector, such as a spectrometer. The detector forms an image of the target object accordingly or otherwise processes the portion. A diffractive element which spectrally disperses or otherwise encodes the illumination light or the portion thereof from the target object is optionally placed mounted on the tip of the light transmission path arrangement and/or the light collection path arrangement. The light transmission path arrangement and said light collection path arrangement are optically isolated from one another, for example by designated sheaths.

According to some embodiments of the present invention there is provided a method of imaging a target object. The method is based on guiding a microcatheter or any other conducting tool having a light collection path arrangement therealong and a diffractive element mounted on its tip to a target space, such as an intrabody space or an inner space of an inspected system or device, via one or more lumens and/or apertures. This allows propagating light, optionally broadband, toward the target object in the target space via a light transmission path arrangement and using the diffractive element for spectrally disperse the light and/or the passing through light and/or reflection of the light from the target surface. For brevity, light received from the object, for example reflected therefrom, passing therethrough, or a emitted therefrom, for example by a fluorescence, may be referred to herein as a reflection. Now, the reflection is propagated in the light collection path arrangement to a detector which forms an image of the target object accordingly. The light transmission path arrangement and the light collection path arrangement are optically isolated from one another, as outlined above and described below.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Reference is now made to FIG. 1, which is a schematic illustration of a spectrally encoded imaging device 100 with light transmission and collection path arrangements 101, 102 which are optically separated from one another, according to some embodiments of the present invention. The device may be used as a fiberscope, an endoscope, and/or a borescope.

Optionally, the light transmission path arrangement 101 includes a light transmission waveguide 110, such as multi or mono mode optical fibers or a fiber bundle, for propagating light to illuminate a target surface 107. Optionally, the light is emanated from a radiation source 102, such as a coherent light source, for example a broadband light source 102, such as a broadband titanium sapphire laser source of Femtolasers Rainbow™ having a bandwidth of 300 nanometer (nm) and a center wavelength of 800 nm fibers, which the specification thereof is incorporated herein by reference. The light collection path arrangement 102 includes a light collection waveguide 113 for propagating a reflection of a portion of the light, optionally spectrally encoded, which may be referred to as wavelength-encoded, from the target surface 107 to a detector 112, such as a spectrometer. The detector 112 optionally forms an image of the target surface 107 from the spectrally encoded reflection. As used herein, the detector 112 may refer to one or more detectors. The waveguides 110, 113 are optically isolated from one another. Optionally, any of the waveguides 110, 113 is a separate optical fiber, for example waveguide 113 could be realized by a Corning HI 780 optical fiber, which the specification thereof is incorporated herein by reference.

According to some embodiments of the present invention, the spectrally encoded imaging device 100 is set to image intrabody surfaces, such as internal organ or tissue surfaces. In such an embodiment, the waveguides 110, 113 are guided via intrabody tubular lumens to evaluate intrabody areas such as the head and the neck. For example, the device 100 may be used as an endoscope or a bronchoscope, for example for rhinoscopy, bronchoscopy, nasopharyngoscopy, laryngoscopy, and/or nasolaryngoscopy procedures, and/or as a borescope for performing inspection work where the area to be inspected is inaccessible by other means, for example visual inspection of aircraft engines, aeroderivative industrial gas turbines, steam turbines, diesel engines, and/or automotive and truck engines. Optionally, the waveguides 110, 113 are two optically separated optical fibers placed in a common flexible tube. The dots in numeral 117 indicate that the waveguides 110, 113 may be of any length.

Optionally, a diffractive element 116 is mounted on the tip of the light collection waveguide 113 to encode spectrally the reflections from the surface of the target object 107. The diffractive element 116 is optionally a grating placed to spectrally disperse the broadband light toward an imaged surface of a target object 107, such as a tissue surface and the like. An example for a possible grating is a 500-2000 lines/mm transmission diffraction grating (G1). Diffractive element 116 may be slanted in relation to the main axis of the light collection waveguide 113 so as to allow linear angular dispersion and minimize optical aberration. Optionally, a collimating optical arrangement 118 of one or more collimating lenses is placed to collimate the light received via the diffractive element 301. Optionally, an imaging optical arrangement 119 of one or more lenses is placed to direct the light received from the target object 107 toward the diffractive element 116.

When the light source 102 is a broadband, spatially incoherent source, the speckle noise of images captured by the imaging device 100 is relatively low. As the speckle noise may be reduced or eliminated, noticeable reductions in apparent resolution, deterioration in the image contrast, and/or a reduction of fine details imaging may be respectively reduced or eliminated.

In addition, the spectral encoding scheme in both the illumination and detection optical path arrangements limits the system's ability to detect signals of different excitation and emission wavelengths, such as fluorescence, photoluminescence and color imaging. By using a spectral encoding scheme in which only the path arrangements is wavelength encoded, the ability to detect signals of different excitation and emission wavelengths, such as fluorescence and photoluminescence is increased.

It should be noted that in some of the used fiberscopes a double clad fiber having core and inner cladding waveguides is utilized. In such fiberscopes, the illumination and reflection path arrangements are within a single fiber. These fiberscopes are often sensitive to back reflections from the fiber interfaces and from the imaging optics.

Figure 2:
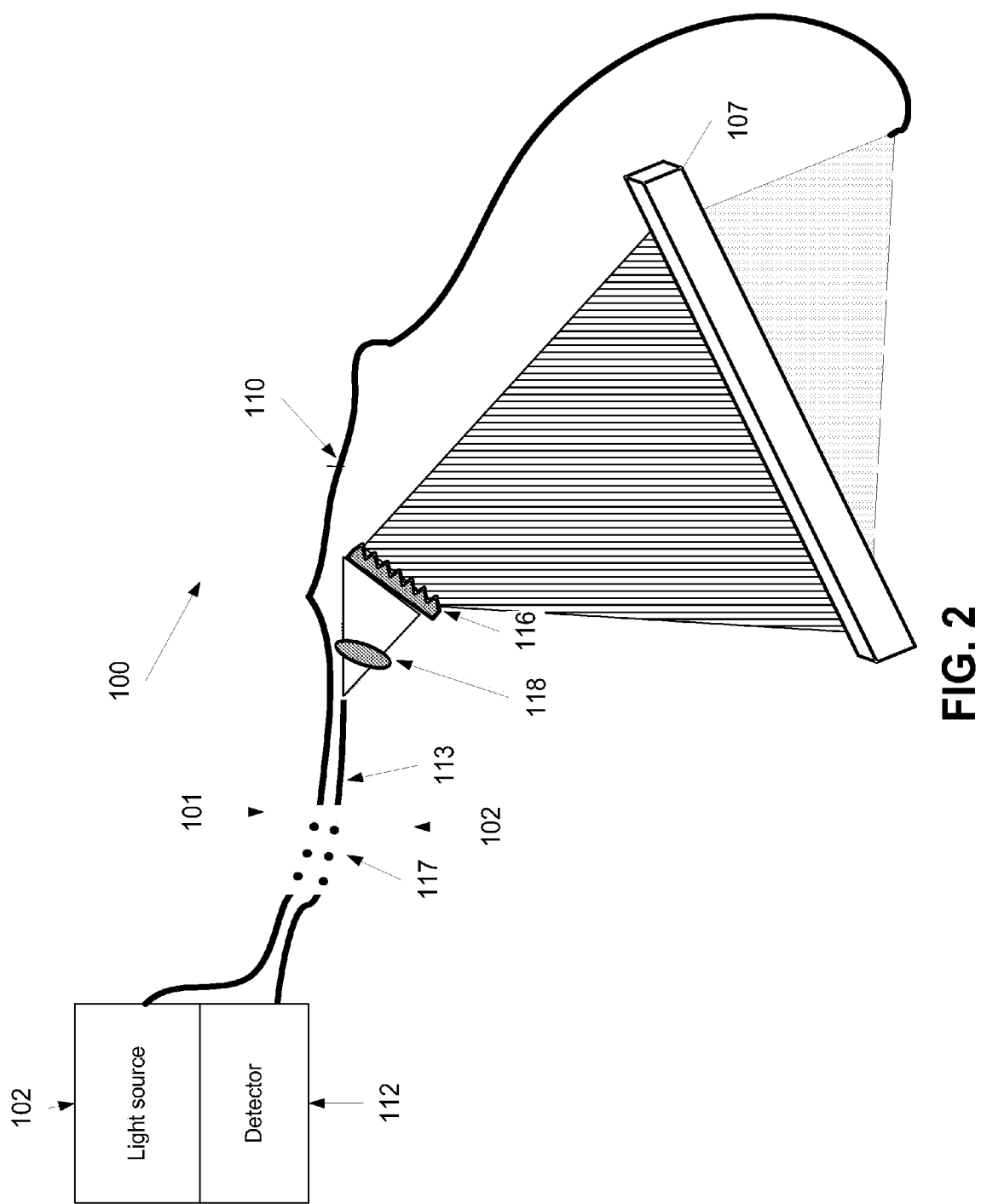
FIG. 2 is a schematic illustration of another spectrally encoded imaging device for back illumination, according to some embodiments of the present invention.

Reference is now also made to FIG. 2, which is a schematic illustration of another spectrally encoded imaging device 200, according to some embodiments of the present invention. The device has similar light transmission and collection path arrangements 101, 102 which are optically separated from one another, as depicted in FIG. 1. However, in FIG. 2, the light transmission waveguide 110 is set to illuminate the back of the target object 107. In such embodiments, the light collection waveguide 113 may collect portion of the illuminating light which passes through the target object 107 and/or from around its outline. The collected light is spectrally dispersed and propagated to the detector 112, similarly to the described above.

Figure 3:
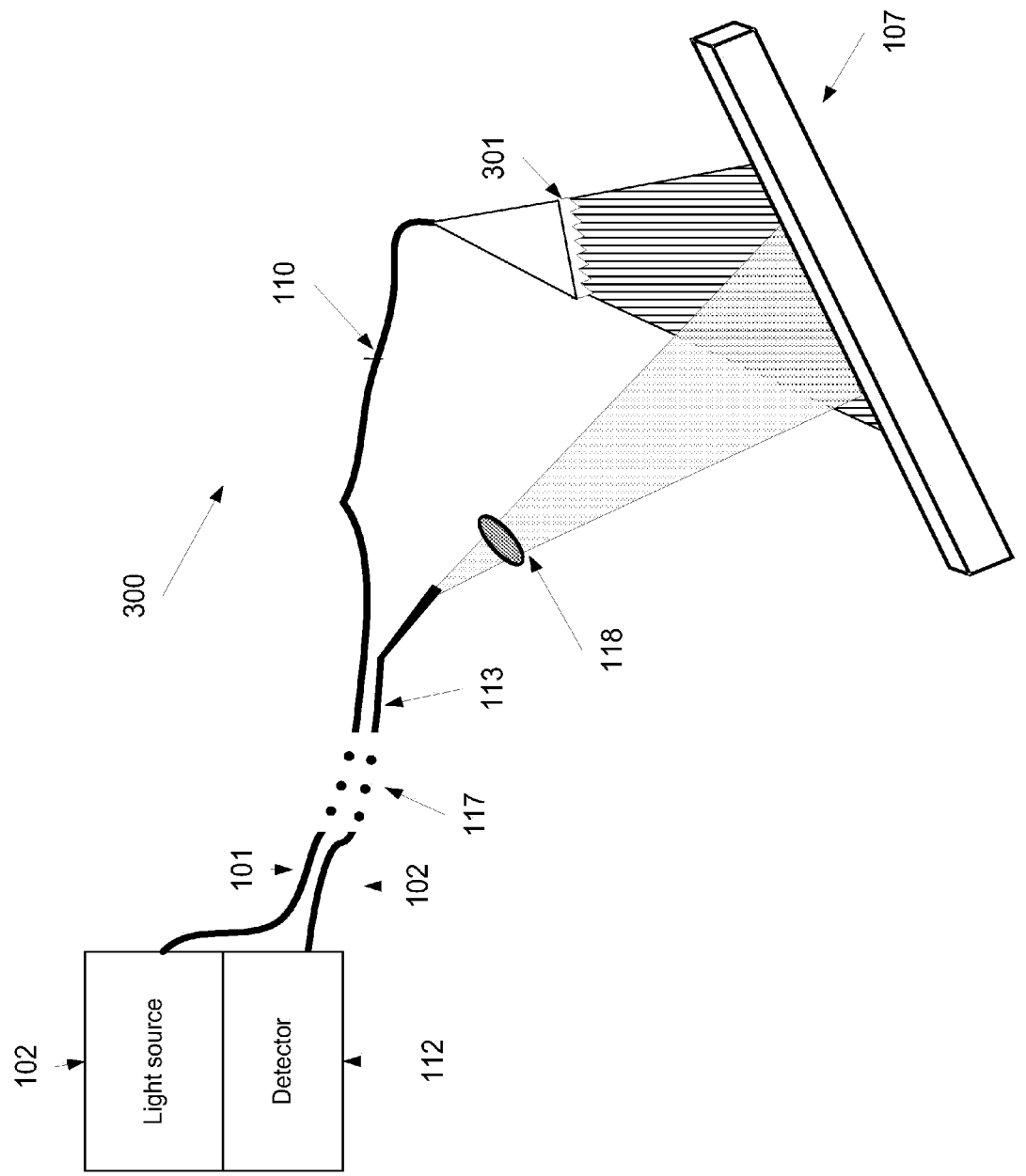
FIG. 3 is a schematic illustration of another spectrally encoded imaging device where the illuminating light is spectrally encoded before hitting the imaged object, according to some embodiments of the present invention.

Reference is now also made to FIG. 3, which is a schematic illustration of another spectrally encoded imaging device 300, according to some embodiments of the present invention. According to some embodiments of the present invention, as shown in FIG. 3, the light emitted from the light transmission waveguide 110 is spectrally encoded, for example by a diffractive element 301, such as a grating, mounted on the tip of the light transmission waveguide 110. In such a manner a broadband light is used for illuminating the target object 107.

Optionally, the light used for illuminating the target object 107, as described above, may be a broadband light. Alternatively, the light may be a narrowband light. In such an embodiment, the target object 107 optionally include fluorescence materials that emit broadband light. The broadband light which impinges the diffractive element 116 is spectrally encoded, as described above, and propagated toward the detector 112 for spectral analysis.

Figure 4:
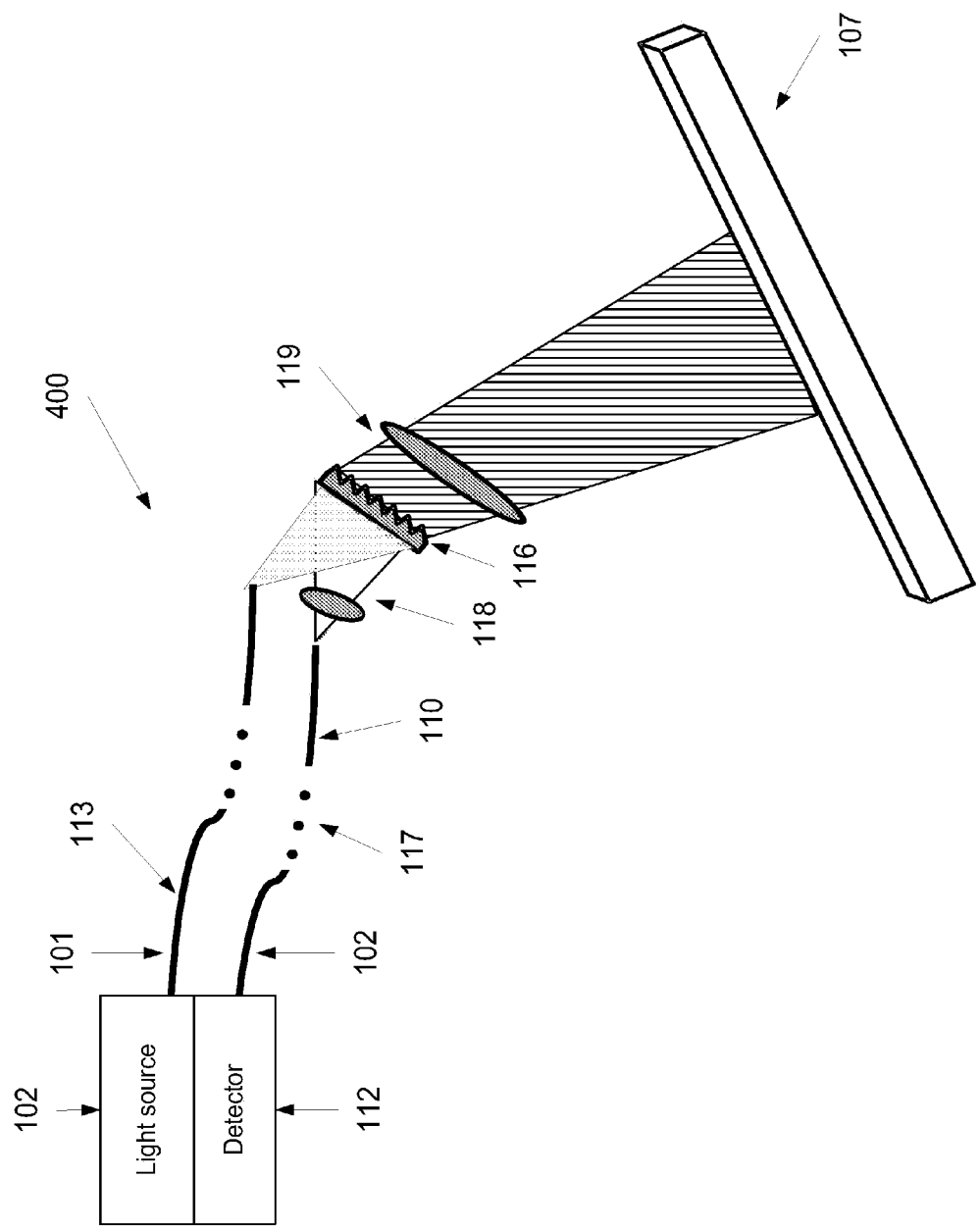
FIG. 4 is a schematic illustration of another spectrally encoded imaging device where the illuminating light is spectrally encoded before and after hitting the imaged object, according to some embodiments of the present invention.

Reference is now also made to FIG. 4, which is a schematic illustration of another spectrally encoded imaging device 400, according to some embodiments of the present invention. The device has similar light transmission and collection path arrangements 101, 102 which are optically separated from one another, as depicted in FIG. 1. However, in FIG. 4, the diffractive element 116 is mounted in front the tips of both the waveguides 110, 113. In such an embodiment, both the illuminating light and the collected reflection are spectrally encoded as the light from the light transmission path arrangement 101 is spectrally dispersed before it illuminates the target object 107.

Figure 5:
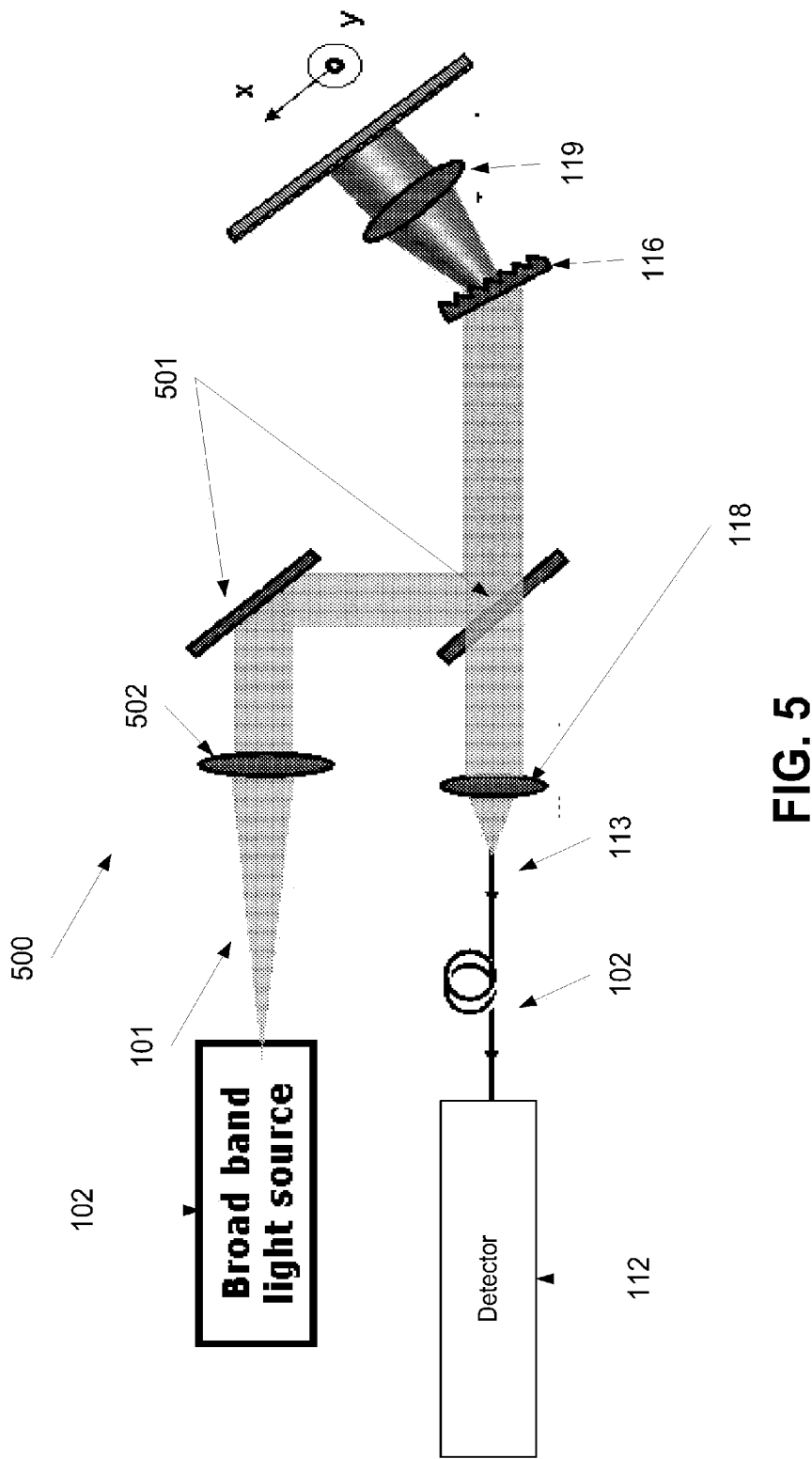
FIG. 5 is a schematic illustration of another spectrally encoded imaging device where the illuminating light directed using an optical arrangement of mirrors and/or half mirrors, according to some embodiments of the present invention.
Figure 6:
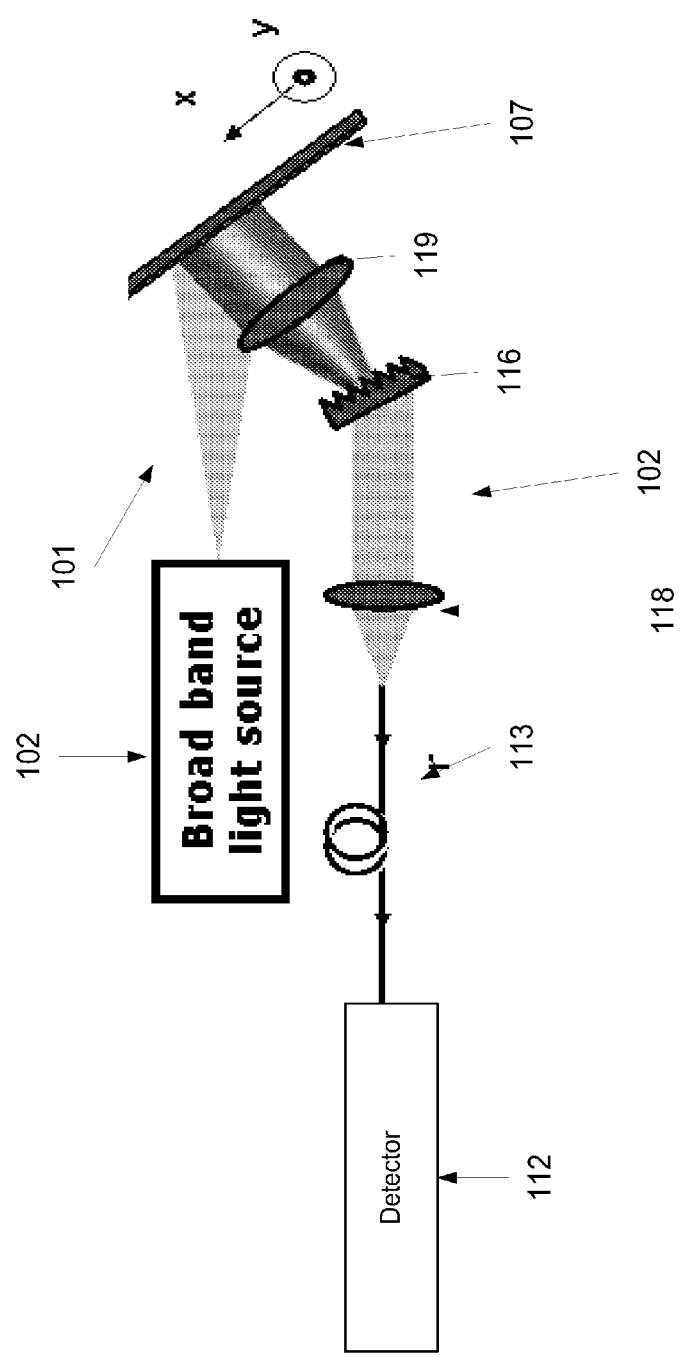
FIG. 6 is a schematic illustration of another spectrally encoded imaging device where the illuminating light directly applied, according to some embodiments of the present invention.
Figure 7:
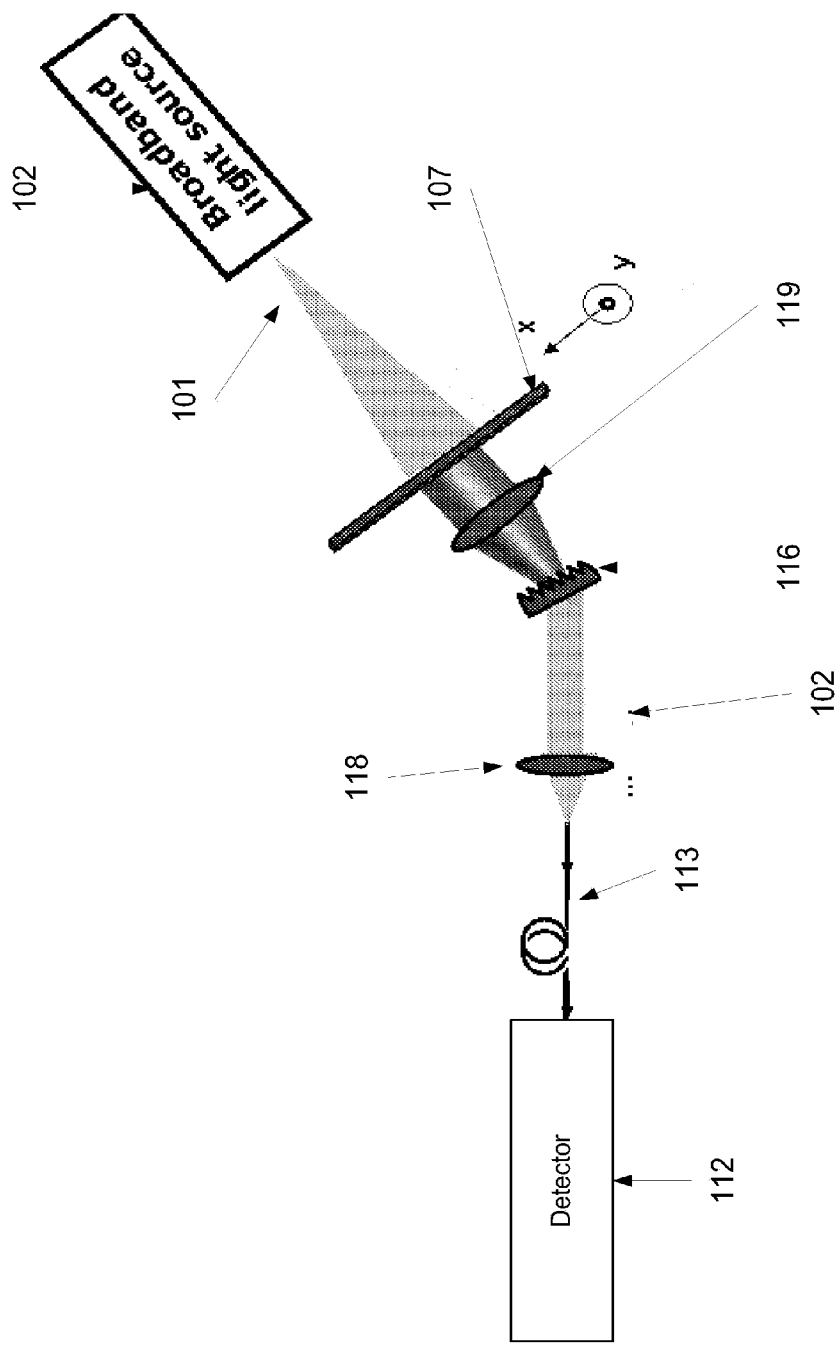
FIG. 7 is a schematic illustration of another spectrally encoded imaging device where the illuminating light directly applied onto the back of the object, according to some embodiments of the present invention.

Reference is now also made to FIG. 5, which is a schematic illustration of another spectrally encoded imaging device 500, according to some embodiments of the present invention. The device has similar light transmission and collection path arrangements 101, 102 which are optically separated from one another, as depicted in FIG. 1. However, in FIG. 5, no light transmission waveguide is used but rather the illumination source 102 is placed closer to the imaged target object 107. In addition, an optical arrangement of mirrors and/or half mirrors 501 is used to direct the illuminating light emitted from the light source 102. The directing is optionally so that the illuminating light passes via the same axis on which light is reflected from the object and passed to the detector 112. As shown in FIG. 5, the light emitted from the light source 102 is not conducted via a waveguide, such as an optical fiber, but rather directed via the arrangement of mirrors 501 toward the diffractive element 116. Optionally, the light is collimated using a collimating optical arrangement 502. In such an embodiment, both the illuminating light and the collected reflection are spectrally encoded as the light from the optical arrangement of mirrors 501 is spectrally dispersed before it illuminates the target object 107. Optionally, the light source 102 is a miniature broadband light source 102 placed at the tip of the imaging device or in proximity thereto. For example, the miniature broadband light source 102 may be a miniature laser diode module, such as the VLM3 670 nm 4 mW E diode laser modules of Coherent™ which the specification thereof is incorporated herein by reference. In such an embodiment, the miniature diode laser module may be connected to a cord which provides power thereto. The cord may be attached along the light collection waveguide 113, facilitating the powering of the miniature broadband light source 102. The light source 102 is guided, together with the tip of the light collection waveguide 113, into an intrabody target space for imaging an intrabody surface, such as a tissue surface. It should be noted that equipping the device with the miniature broadband light source 102 and optionally with the optical arrangement of mirrors 501 may be done as known in the art. It should be noted that the illumination source 102 may illuminate the target object 107 directly, for example as shown at FIG. 6. The illumination source 102 may directly illuminate the target object 107 from the back, for example as shown at FIG. 7.

Optionally, the target object 107 may include fluorescence materials as described above. In such an embodiment, when the target object 107 is an intrabody object or placed in an inner space of an inspected system or device, the light source 102 may be an external light source which is not conducted via lumens in the body of the patient and/or in the lumens of an inspected system or device. The external light source excites the fluorescence materials by illuminating them via the skin and/or any other tissue or cover. Optionally, the target object 107 is excited by any other electromagnetic radiation source. For example, the fluorescence materials may be excited by induction. In such an embodiment, the spectrally encoded imaging device does not include a light transmission path as the exciting radiation is provided from an external source.

Figure 8:
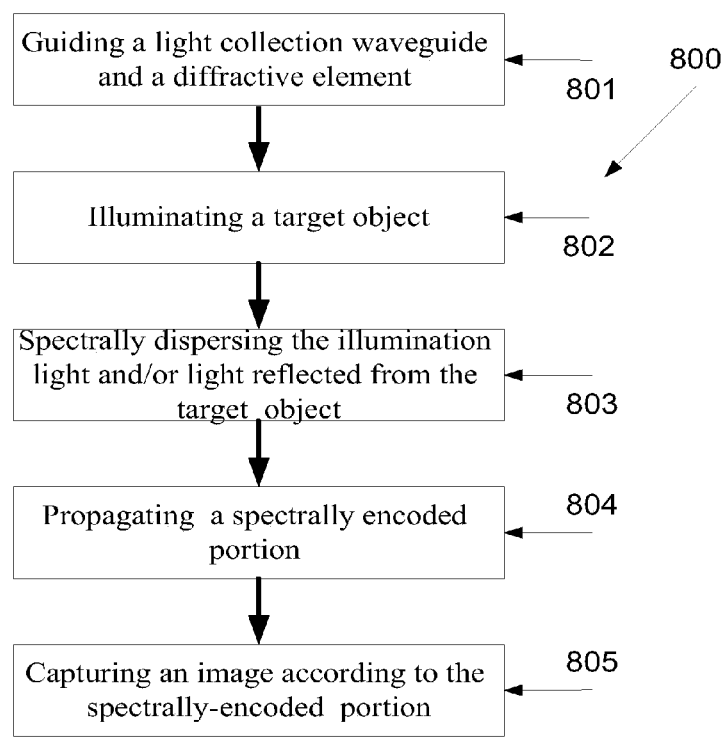
FIG. 8 is a flowchart of a method of spectrally encoded imaging of an object, such as a target surface, according to some embodiments of the present invention.

Reference is now made to FIG. 8, which is a flowchart 800 of a method of spectrally encoded imaging of an object, such as a target surface, according to some embodiments of the present invention. First, as shown at 801, the tip of a guiding tool, such as a microcatheter, having a light collection path arrangement, such as 102, is guided to an intrabody target area or an examination space in an inspected element, via one or more body tubular lumens or tubular passages of the inspected element. The tip has at least one diffractive element, such as 116, mounted on its tip. For example, the guiding tool 100 may be guided as an endoscope or a bronchoscope, for example for rhinoscopy, nasopharyngoscopy, laryngoscopy, and/or nasolaryngoscopy procedures, and/or as a borescope for performing inspection work where the area to be inspected is inaccessible by other means, for example visual inspection of aircraft engines, aeroderivative industrial gas turbines, steam turbines, diesel engines, and/or automotive and truck engines.

Now, as shown at 802, light is propagated toward a target surface in said intrabody target area, optionally via a light transmission path arrangement, for example via a multi mode optical fiber or from a miniature light source which is attached in, or in proximity, to the tip. Now, as shown at 803 the illuminating light and/or the light reflected from the target object 107 is spectrally dispersed, for example using the diffractive element 116. The spectrally encoded reflection is now propagated in the light collection path arrangement to a detector, as shown at 804, for example as described above. This allows, as shown at 805, forming an image of the target surface according to the spectrally encoded reflected light. In this method, the light transmission path arrangement and the light collection path arrangement are optically isolated from one another.

It is expected that during the life of a patent maturing from this application many relevant systems and methods will be developed and the scope of the term a light source and a waveguide is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of imaging a target object, comprising:
   maneuvering a light collection optical fiber to a target space;
   propagating incident light towards said target object in said target space through a light transmission path;
   propagating an optical stream of light received from within a region of said target which is illuminated by said incident light, through said light collection optical fiber to a detector, said light collection optical fiber being physically separated and optically isolated from said light transmission path;
   spectrally diffracting using a diffraction element disposed in the region of said target space, at least one of said incident light and said received light, such that said optical stream of received light propagated through said light collection optical fiber is spectrally encoded; and
   forming a representation of an image of said target object by impingement of said optical stream of received light on said detector.

2. The method of claim 1, wherein said target space is an intrabody space, and said target object is a tissue surface.

3. The method of claim 1, wherein said propagating incident light comprises transmitting said incident light down an optical waveguide into said target space.

4. The method of claim 1, wherein said propagating incident light comprises directly illuminating said target object using a source located within said target space.

5. The method of claim 1, wherein said method is performed during a procedure selected from a group consisting of: endoscopy, bronchoscopy, rhinoscopy, nasopharyngoscopy, laryngoscopy, and nasolaryngoscopy.

6. The method of claim 1, wherein said light received from said target comprises either incident light reflected from said target or incident light transmitted through said target or fluorescence emission from said target object resulting from illumination thereof by said incident light.

7. The method of claim 1, wherein said incident light is broadband light.

8. The method of claim 1, wherein said incident light is generated from a miniature light source disposed within said target space.

9. The method of claim 1, wherein said light transmission path comprises an illuminating optical fiber for propagating said incident light from a source located distally remote from said target space, to illuminate said target object.

10. A spectrally encoded imaging device, comprising:
    a light transmission path which propagates incident light to illuminate a target object;
    a light collection optical fiber, physically separated and optically isolated from said light transmission path, propagating to a detector, a spectrally encoded optical stream of light received from within a region of said target object which is illuminated by said incident light, said spectrally encoded optical stream of light impinging on said detector to generate a representation of said image of said target object at said detector; and
    a diffractive element which spectrally diffracts at least one of said incident light and said portion of received light from said region of said target object,
    wherein said diffractive element is disposed at a distal region of said spectrally encoded imaging device.

11. A spectrally encoded imaging device according to claim 10, wherein said spectrally encoded light comprises either part of said incident light reflected from said target object, or part of said incident light transmitted through said target object, or fluorescence emission from said target object resulting from illumination thereof by said incident light.

12. A spectrally encoded imaging device according to claim 10, wherein said incident light is generated from a broadband light source.

13. A spectrally encoded imaging device according to claim 10, wherein said incident light is generated from a light source disposed at the distal end region of said imaging device.

14. A spectrally encoded imaging device according to claim 10, wherein said light transmission path comprises an illumination optical fiber for propagating said incident light from a source located at the proximal end of said device, to illuminate said target object.

15. A spectrally encoded imaging device according to claim 14, wherein said diffractive element is a grating slanted in relation to the axis of said optical fiber.

16. A spectrally encoded imaging device according to claim 10, wherein said light collection optical fiber is positioned to collect said spectrally encoded light received from said target object, and said incident light illuminating said target through said light transmission path is spectrally encoded.

17. A spectrally encoded imaging device according to claim 10, wherein said incident light is narrowband light and said target object comprises a fluorescence material which emits broadband light when excited by said narrowband light.

18. A spectrally encoded imaging device according to claim 10, wherein said light transmission path is external to an intrabody space confining said target object.

19. A spectrally encoded imaging device according to claim 10, wherein said incident light propagated along said transmission path is spectrally encoded.

* * * * *